(12) United States Patent
Chung et al.

(10) Patent No.: US 8,106,071 B2
(45) Date of Patent: Jan. 31, 2012

(54) COMPOSITIONS FOR TREATING HYPERPROLIFERATIVE VASCULAR DISORDERS AND CANCERS

(75) Inventors: Kwang Hoe Chung, Seongnam-si (KR); Chwang Siek Pak, Daejeon (KR); Sung Yu Hong, Seoul (KR); Soo Jung Kang, Seoul (KR); Young Doug Sohn, Yongin-si (KR); Jae Hoon Hwang, Seoul (KR); Eun Bok Choi, Daejeon (KR); Gyu Hwan Yon, Daejeon (KR); Hyeon Kyu Lee, Daejeon (KR); Heui Cheol Yang, Daejeon (KR)

(73) Assignee: Biobud Co., Ltd., Seoul (KR)

( * ) Notice: Subject to any disclaimer, the term of this patent is extended or adjusted under 35 U.S.C. 154(b) by 0 days.

(21) Appl. No.: 12/528,224

(22) PCT Filed: May 23, 2007

(86) PCT No.: PCT/KR2007/002512
§ 371 (c)(1),
(2), (4) Date: Aug. 21, 2009

(87) PCT Pub. No.: WO2008/102932
PCT Pub. Date: Aug. 28, 2008

(65) Prior Publication Data
US 2010/0120849 A1     May 13, 2010

(30) Foreign Application Priority Data

Feb. 21, 2007 (KR) ........................ 10-2007-0017281
Feb. 21, 2007 (KR) ........................ 10-2007-0017282

(51) Int. Cl.
*A01N 43/42*     (2006.01)
(52) U.S. Cl. ........................ 514/311; 514/312
(58) Field of Classification Search .................. None
See application file for complete search history.

(56) References Cited

FOREIGN PATENT DOCUMENTS
WO    WO 02081728 A2 * 10/2002

* cited by examiner

Primary Examiner — Sreeni Padmanabhan
Assistant Examiner — Svetlana M Ivanova
(74) Attorney, Agent, or Firm — Clark & Elbing LLP (57) ABSTRACT

The present invention relates to a method for treating or reducing the development of a hyperproliferative disorder, which comprises administering to a subject a composition, which comprises as an active ingredient the compound represented by the Formula 1:

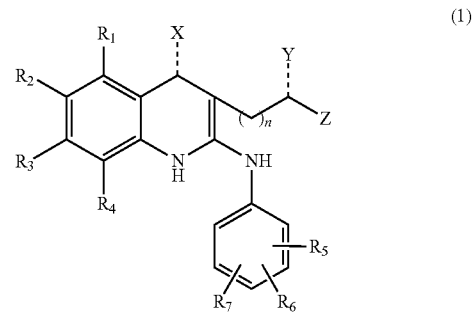

(1)

wherein $R_1$, $R_2$, $R_3$, $R_4$, $R_5$, $R_6$ and $R_7$ independently represent hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

X and Y independently represent hydrogen, oxygen, or sulfur, bound to a carbon atom via a single or double bond;

Z represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl, alkylaryl or —NH—$R_8$;

$R_8$ represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

n is an integer of 0-3.

2 Claims, 1 Drawing Sheet

COMPOSITIONS FOR TREATING HYPERPROLIFERATIVE VASCULAR DISORDERS AND CANCERS

CROSS-REFERENCE TO RELATED APPLICATIONS

This application claims priority under 35 U.S.C. §371 from international application PCT/KR2007/002512, filed May 23, 2007, which claims priority from Korean Patent Application No. 10-2007-0017281, filed Feb. 21, 2007 and Korean Patent Application No. 10-2007-0017282, filed Feb. 21, 2007.

BACKGROUND OF THE INVENTION

1. Field of the Invention

The present invention relates to a composition for preventing or treating hyperproliferative vascular disorders by inhibiting proliferation of vascular smooth muscle cells and an anticancer composition.

2. Description of the Related Art

Cardiovascular disease was responsible for about 10% of mortality causes in early the 20$^{th}$ century and is now for about 50% of mortality causes in advanced countries and for about 25% of mortality causes in developed countries. Arteriosclerosis, one of the most incidental cardiovascular diseases, is developed due to vascular lesions or malfunction of vascular endothelial cells caused by various conditions such as smoking and diabetic symptoms. The arteriosclerotic plaque formation and thrombogenesis prevent blood supply to each organ to ultimately generate serious symptoms. Although arteriosclerotic vessels are occasionally treated by surgical intervention such as balloon dilatation or stent implantation, postoperative restenosis is likely to occur with about 30% incidence (*Pharmacol, Ther.* 2001, 92, 165-178).

To treat arteriosclerosis (particularly, artherosclerosis) and restenosis, a multitude of substances to inhibit proliferation or migration of vascular smooth muscle cells have been suggested. For example, heparin has been reported to inhibit proliferation of smooth muscle cells after angioplasty (Buchwald et al., *J. Cardiovasc. Pharmacol.*, 28:481-487(1996)).

U.S. Pat. Nos. 5,498,775 and 5,464,827 disclose polyanionic benzylglycoside or cyclodextrin as inhibitors to proliferation of smooth muscle cells. WO 96/14325 discloses acylated benzylglycoside as inhibitors to proliferation of smooth muscle cells.

A variety of therapies for cancers have been already proposed, including chemotherapy, radiotherapy, gene therapy and natural substances-implicated therapy.

Among chemotherapeutics so far developed, alkylating agents including cyclophosphamide and busulfan exhibit their anticancer effects by the formation of covalent bonds with nitrogen atoms on DNA nucleotides due to their strong electrophilic properties. Metabolic antagonists such as 5-fluoruracil contain vitamins, amino acids and nucleotides in their structures and inhibit enzymes involved in nucleic acid biosynthesis or incorporate into DNA or RNA molecules, thereby inhibiting cell growth and proliferation. Furthermore, antibiotics-typed anticancer drugs such as adriamycin inhibit the inherent functions of DNA to exhibit their therapeutic effects.

Korean Pat. No. 433679 describes 4'-demethyl-4'-O-substituted-1-deoxypodophyllotoxin derivates as anticancer drugs and Korean Pat. No. 589967 suggests 3-amino-6-methyl-indazol derivatives as anticancer drugs.

Furthermore, Korean Pat. No. 361480 discloses novel use of micrococcin as anticancer agents, Korean Pat. No. 548921 describes furanquinone derivatives having anticancer activities and Korean Pat. No. 420007 anthracycline derivatives and pharmaceutical anticancer composition containing the same.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventor have made intensive researches to develop novel compounds to effectively inhibit proliferation of vascular smooth muscle cells and cancer cells, hereby ensuring prevention or treatment of hyperproliferative vascular disorders such as arteriosclerosis and restenosis, and cancers. As results, we have discovered compounds to serve as chemotherapeutic agents for the above-described two types of diseases.

Accordingly, it is an object of this invention to provide a composition for inhibiting proliferation of smooth muscle cells.

It is another object of this invention to provide a pharmaceutical composition for preventing or treating hyperproliferative vascular disorders.

It is still another object of this invention to provide a pharmaceutical anticancer composition.

It is further object of this invention to provide a method for inhibiting proliferation of smooth muscle cells.

It is still further object of this invention to provide a method for preventing or treating hyperproliferative vascular disorders.

It is another object of this invention to provide a method for preventing or treating cancers.

Other objects and advantages of the present invention will become apparent from the following detailed description together with the appended claims and drawings.

In one aspect of this invention, there is provided a composition for inhibiting proliferation of smooth muscle cells, which comprises as an active ingredient the compound represented by the Formula 1:

wherein $R_1$, $R_2$, $R_3$, $R_4$, $R_5$, $R_6$ and $R_7$ independently represent hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

X and Y independently represent hydrogen, oxygen, or sulfur, bound to a carbon atom via a single or double bond;

Z represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl, alkylaryl or —NH—$R_8$;

$R_8$ represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

n is an integer of 0-3.

In another aspect of this invention, there is provided a pharmaceutical composition for preventing or treating hyperproliferative vascular disorders, which comprises (a) a pharmaceutically effective amount of the compound represented by the Formula 1; and (b) a pharmaceutically acceptable carrier.

(1)

wherein $R_1$, $R_2$, $R_3$, $R_4$, $R_5$, $R_6$ and $R_7$ independently represent hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

X and Y independently represent hydrogen, oxygen, or sulfur, bound to a carbon atom via a single or double bond;

Z represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl, alkylaryl or —NH—$R_8$;

$R_8$ represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

n is an integer of 0-3.

In still another aspect of this invention, there is provided a pharmaceutical anticancer composition, which comprises (a) a pharmaceutically effective amount of the compound represented by the Formula 1; and (b) a pharmaceutically acceptable carrier:

(1)

wherein $R_1$, $R_2$, $R_3$, $R_4$, $R_5$, $R_6$ and $R_7$ independently represent hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

X and Y independently represent hydrogen, oxygen, or sulfur, bound to a carbon atom via a single or double bond;

Z represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl, alkylaryl or —NH—$R_8$;

$R_8$ represents hydrogen, halo, hydroxyl, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl;

n is an integer of 0-3.

In further aspect of this invention, there is provided a method for inhibiting proliferation of smooth muscle cells, which comprises administering to a subject a composition comprising the compound represented by the Formula 1 as an active ingredient.

In still further aspect of this invention, there is provided a method for preventing or treating hyperproliferative vascular disorders, which comprises administering to a subject a pharmaceutical composition comprising (a) a pharmaceutically effective amount of the compound represented by the Formula 1; and (b) a pharmaceutically acceptable carrier.

In another aspect of this invention, there is provided a method for preventing or treating cancers, which comprises administering to a subject a pharmaceutical composition comprising (a) a pharmaceutically effective amount of the compound represented by the Formula 1; and (b) a pharmaceutically acceptable carrier.

In still another aspect of this invention, there is provided a use of the compound represented by the Formula 1 for manufacturing a medicament for inhibiting proliferation of smooth muscle cells.

In further aspect of this invention, there is provided a use of the compound represented by the Formula 1 for manufacturing a medicament for preventing or treating hyperproliferative vascular disorders.

In still further aspect of this invention, there is provided a use of the compound represented by the Formula 1 for manufacturing a medicament for preventing or treating cancers.

The present inventor have made intensive researches to develop novel compounds to effectively inhibit proliferation of vascular smooth muscle cells and cancer cells, thereby ensuring prevention or treatment of hyperproliferative vascular disorders such as arteriosclerosis and restenosis, and cancers. As results, we have discovered compounds to serve as chemotherapeutic agents for the above-described two types of diseases.

The present compound is defined by the Formula 1. The term used herein "halo" means halogen atoms, for instance including fluoro, chloro, bromo, and iodo, preferably fluoro, chloro or bromo. The term "$C_1$-$C_{12}$ alkyl" is defined herein to be straight chain or branched chain saturated hydrocarbon group from $C_1$ to $C_{12}$, preferably, straight or branched $C_1$-$C_4$ alkyl, i.e., lower alkyl including methyl, ethyl, n-propyl, isopropyl, isobutyl, n-butyl and t-butyl. The term "alkenyl" means a straight or branched unsaturated hydrocarbon chain comprising a designated number of carbon atoms, preferably, $C_2$-$C_6$ straight or branched alkenyl containing 2 to 6 carbon atoms having at least one double bond, for instance, including ethenyl, propenyl, isopropenyl, butenyl, iso-butenyl, t-butenyl, n-pentenyl and n-hexyenyl.

The term "cycloalkyl" used herein refers to cyclic hydrocarbon radicals comprising a designated number of carbon atoms, preferably $C_3$-$C_8$ cycloalkyl, including cyclopropyl, cyclobutyl and cyclopentyl. The term "cycloalkenyl" refers to cyclic hydrocarbon radicals with a designated number of carbon atoms having at least one double bond, preferably $C_5$-$C_7$ cycloalkenyl, including cyclopentene, cyclohexene and cyclohexadiene. The term "alkylamino" means alkyl groups having amino substituents.

The term used herein "aryl" means totally or partially unsaturated, substituted or unsubstituted monocylic or polycyclic carbon rings, preferably monoaryl or biaryl. The monoaryl groups have preferably the carbon number of 5-6, and the biaryl groups have preferably the carbon number of 9-10. Most preferably, the aryl group is substituted or unsubstituted phenyl. The monoaryl group, e.g., phenyl may be substituted with various substituents, preferably halo, hydroxy, nitro, cyano, straight or branched, substituted or unsubstituted $C_1$-$C_4$ alkyl, straight or branched $C_1$-$C_4$ alkoxy, alkyl-substituted sulfanyl, phenoxy, $C_3$-$C_6$ cycloheteroalkyl or substituted or unsubstituted amino groups. The term "alkoxy" means —O alkyl groups. Where substituted with $C_1$-$C_4$ substituted alkyl groups, halo preferably chloro or fluoro, more preferably fluoro substituted alkyl substituents may be used.

Where R or Z is biary, e.g. naphthyl, it may be substituted in various positions with various substituents, preferably halo, hydroxy, nitro, cyano, straight or branched, substituted or unsubstituted $C_1$-$C_4$ alkyl, straight or branched $C_1$-$C_4$ alkoxy, or substituted or unsubstituted amino groups, more preferably alkyl-substituted amino groups.

The term "heteroaryl" means heterocyclic aromatic groups containing heteroatoms such as N, O and S. Preferably, the heteroaryl is heterobiaryl containing N atom as hetereoatoms.

The term "arylalkyl (aralkyl)" means aryl groups linked to a structure comprised of one or more alkyl groups, e.g. benzyl. The term "alkylaryl" means alkyl groups linked to a structure comprised of one or more aryl groups. The "arylalkenyl" means aryl groups linked to a structure comprised of one or more alkenyl groups, e.g. phenylethenyl.

According to a preferred embodiment, $R_1$, $R_2$, $R_3$, $R_4$, $R_5$, $R_6$ and $R_7$ independently represent hydrogen, halo, nitro or $C_1$-$C_{12}$ alkyl. Where $R_1$, $R_2$, $R_3$, $R_4$, $R_5$, $R_6$ and/or $R_7$ is alkyl group, it is preferably straight or branched $C_1$-$C_4$ alkyl group.

According to a preferred embodiment, n is 0 or 1, most preferably 0.

In the Formula 1, the position of X and/or Y may be occupied by oxygen or sulfur atom, most preferably oxygen atom.

According to a preferred embodiment, Z represents $C_1$-$C_{12}$ alkyl or —NH—$R_8$; and $R_8$ represents an unsubstituted or substituted phenyl group.

According to a preferred embodiment, the compound of the present invention is represented by the following Formula 2:

(2)

wherein $R_1$, $R_2$, $R_3$, $R_4$, $R_5$, $R_6$ and $R_7$ independently represent hydrogen, halo, nitro or $C_1$-$C_{12}$ alkyl; Z represents hydrogen, hydroxyl, $C_1$-$C_{12}$ alkyl, $C_3$-$C_8$ cycloalkyl, $C_1$-$C_6$ alkylamino, $C_1$-$C_6$ alkoxy, aryl, heteroaryl, arylalkyl, alkylaryl or —NH—$R_8$; and $R_8$ represents hydrogen, carboxyl, $C_1$-$C_{12}$ alkyl, $C_3$-$C_8$ cycloalkyl, $C_1$-$C_6$ alkylamino, $C_1$-$C_6$ alkoxy, aryl, heteroaryl, arylalkyl or alkylaryl.

According to a preferred embodiment, the compound of the present invention is represented by the following Formula 3:

(3)

wherein $R_1$, $R_2$, $R_3$, $R_4$, $R_5$, $R_6$ and $R_7$ independently represent hydrogen, halo, nitro or $C_1$-$C_{12}$ alkyl.

More preferably, the compound used in the present composition is represented by the following Formula 4:

(4)

wherein $R_1$, $R_2$, $R_3$, $R_4$, $R_5$, $R_6$ and $R_7$ independently represent hydrogen, halo, nitro or $C_1$-$C_{12}$ alkyl.

Still more preferably, the compound used in the present composition is selected from compounds of the Formula 4 having substituents indicated in Table 1:

TABLE 1

| $R_1$ | $R_2$ | $R_3$ | $R_4$ | $R_5$ | $R_6$ | $R_7$ |
|---|---|---|---|---|---|---|
| Br | H | Br | H | H | H | Br |
| H | Cl | H | —$NO_2$ | Cl | H | Br |
| —$CH_3$ | H | H | Cl | F | F | F |
| H | F | H | F | F | F | F |
| —$CH_3$ | H | H | Cl | Cl | H | F |
| H | H | H | —$NO_2$ | H | H | —$CH_3$ |
| H | F | H | F | H | H | F |
| H | H | H | —$CH_3$ | H | Cl | H |
| F | H | H | Cl | H | F | H |
| —$NO_2$ | H | H | Cl | Cl | H | Cl |

More preferably, the compound used in the present composition is represented by the following Formula 5:

(5)

Still more preferably, the compound used in the present composition is selected from compounds of the Formula 5 having substituents indicated in Table 2:

TABLE 2

| $R_5$ | $R_6$ | $R_7$ |
|---|---|---|
| H | H | H |
| Cl | H | Cl |

According to a more preferred embodiment, the compound used in the present composition is represented by the following Formula 6:

(6)

Still more preferably, the compound used in the present composition is selected from compounds of the Formula 6 having substituents indicated in Table 3:

TABLE 3

| $R_5$ | $R_6$ | $R_7$ |
|---|---|---|
| F | H | Cl |
| Cl | Cl | H |
| H | F | F |

Still yet more preferably, the compounds useful in the present composition are compounds of the Formula 4 in which $R_1$ is H, $R_2$ is Cl, $R_3$ is H, $R_4$ is —$NO_2$, $R_5$ is Cl, $R_6$ is H, and $R_7$ is Br; compound in which $R_1$ is —$CH_3$, $R_2$ is H, $R_3$ is H, $R_4$ is Cl, $R_5$ is F, $R_6$ is H, and $R_7$ is F; and compound in which $R_1$ is H, $R_2$ is F, $R_3$ is H, $R_4$ is Cl, $R_5$ is F, $R_6$ is F, and $R_7$ is F; compounds of the Formula 5 in which $R_5$ is H, $R_6$ is H, and $R_7$ is H; and $R_5$ is Cl, $R_6$ is H, and $R_7$ is Cl; and compounds of the Formula 6 in which $R_5$ is F, $R_6$ is H, and $R_7$ is Cl; $R_5$ is Cl, $R_6$ is Cl, and $R_7$ is H; and $R_5$ is H, $R_6$ is F, and $R_7$ is F.

Most preferably, the compounds useful in the present composition are compounds of the Formula 4 in which $R_1$ is H, $R_2$ is Cl, $R_3$ is H, $R_4$ is —$NO_2$, $R_5$ is Cl, $R_6$ is H, and $R_7$ is Br; compound in which $R_1$ is —$CH_3$, $R_2$ is H, $R_3$ is H, $R_4$ is Cl, $R_5$ is F, $R_6$ is H, and $R_7$ is F; compounds of the Formula 5 in which $R_5$ is H, $R_6$ is H, and $R_7$ is H; and $R_5$ is Cl, $R_6$ is H, and $R_7$ is Cl.

The compounds of the present invention may contain one or more chiral centers and/or geometrical isomer centers; therefore it could be obvious to one of skill in the art that the present invention encompasses all stereoisomers, optical isomers, diastereomers and geometrical isomers of the Formula 1 having activities to inhibit proliferation of smooth muscle cells.

Exemplified compounds useful in the present invention are described in Examples.

The compounds of the present invention effectively inhibit proliferation of vascular smooth muscle cells and cancer cells, thereby ensuring prevention or treatment of hyperproliferative vascular disorders such as arteriosclerosis and restenosis, and cancers.

The pharmaceutical composition of the present invention is very effective in prevention or treatment of hyperproliferative vascular disorders. The term used herein "hyperproliferative vascular disorders" means diseases or disorders caused by excessive proliferation of vascular cells, in particular, vascular smooth muscle cells. The hyperproliferative vascular disorders comprise various diseases, for example, arteriosclerosis, atherosclerosis, restenosis and stenosis.

Preferably, the hyperproliferative vascular disorders prevented or treated by the pharmaceutical composition of the present invention include arteriosclerosis, atherosclerosis and restenosis. Atherosclerosis is caused by deposition or fibrosis of fatty substances in aortic endothelium. Restenosis is known to be developed by restricted vessel passage after traumatization of vascular walls.

In addition, vessel restenosis developed post-arteriosclerosis and stent insertion have been suggested to be associated with proliferation and migration of vascular smooth muscle cells, and secretion of extracellular matrix (*Circulation*, 1997, 95, 1998-2002; *J. Clin. Invest.* 1997, 99, 2814-2816; and *Cardiovasc. Res.* 2002, 54, 499-502). In this regard, researches for arteriosclerosis and restenosis have been extensively made to provide novel drugs for inhibiting proliferation of vascular smooth muscle cells, and as a result a few chemotherapeutic drugs are now clinically employed (*J. Am. Coll. Cardiol.*, 2002, 39, 183-193). Accordingly, it could be understood that the compounds of the present invention to very effectively inhibit proliferation of vascular smooth muscle cells are promising in treatment of hyperproliferative vascular disorders.

The pharmaceutical composition of the present invention is also effective in prevention or treatment of cancers. Exemplified cancers prevented or treated by the pharmaceutical composition include stomach cancer, lung cancer, breast cancer, ovarian cancer, liver cancer, bronchogenic cancer, nasopharyngeal cancer, laryngeal cancer, pancreatic cancer, bladder cancer, colon cancer, cervical cancer, brain cancer, prostate cancer, bone cancer, skin cancer, thyroid cancer, parathyroid cancer and ureter cancer, but not limited to.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition of this invention may be administered orally or parenterally. For non-oral administration, intravenous injection, subcutaneous injection, intramuscular injection, intraperitoneal injection or transdermal administration may be employed.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Preferably, the pharmaceutical composition of the present invention is administered with a daily dose of 0.001-1000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

As active ingredients in the present composition, they may include compounds represented by the Formula 1, pharmaceutically acceptable salts, hydrates, solvates or prodrugs thereof.

The term used herein "pharmaceutically acceptable salts" means those salts of the Formula 1 which retain pharmacological activities of interest, i.e., activities to inhibit proliferation of vascular smooth muscle cells and cancer cells. These salts may be formed using inorganic acids such as hydrochloride, hydrobromide and hydroiodide, or organic acids such as acetate, adipate, alginate, aspartate, benzoate, benzenesulfonate, p-toluenesulfonate, bisulfate, sulfamate, sulfate, naphthylate, butyrate, citrate, camphorate, camphosulfate, cyclopentanepropionate, digluconate, dodecylsulfate, ethanesulfate, fumarate, glucoheptanoate, glycerophosphate, hemisulfate, heptanoate, hexanoate, 2-hydroxyethanesulfate, lactate, maleate, methanesulfonate, 2-naphthalenesulfonate, nicotinate, oxalate, tosylate and undecanoate.

The term "pharmaceutically acceptable hydrates" means hydrates of the Formula 1 which retain pharmacological activities of interest. The term "pharmaceutically acceptable solvates" refers to solvates of the Formula 1 which retain pharmacological activities of interest. The hydrates and solvates may be prepared using acids described hereinabove.

The term used herein "pharmaceutically acceptable prodrugs" means derivates of the Formula 1 which require bioconversion reactions for exhibiting pharmacological activities of interest. These prodrugs are generally prepared for chemical stability, patient compliance, bioavailability, organ selectivity, prescription convenience, sustained release and decrease of adverse effects. The synthesis of prodrugs may be carried out using compounds of the Formula 1 according to conventional processes (e.g., Burger's Medicinal Chemistry and Drug Chemistry, 5th ed., 1:172-178 and 949-982(1995)).

As demonstrated in Examples the present compounds exhibit $IC_{50}$ values of less than 0.03 μM and 0.16 μM for vascular smooth muscle cells and cancer cells, respectively to effectively prevent proliferation of vascular smooth muscle cells and cancer cells, thereby ensuring prevention or treatment of hyperproliferative vascular disorders such as arteriosclerosis and restenosis, and cancers.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparative Example 1

Compound Preparation 1

The compounds represented by the following Formula 4 were synthesized according to the Scheme 1:

(4)

TABLE 4

| Compound ID | $R_1$ | $R_2$ | $R_3$ | $R_4$ | $R_5$ | $R_6$ | $R_7$ |
|---|---|---|---|---|---|---|---|
| (BD001) | Br | H | Br | H | H | H | Br |
| (BD002) | H | Cl | H | —NO$_2$ | Cl | H | Br |
| (BD003) | —CH$_3$ | H | H | Cl | F | F | F |
| (BD004) | H | F | H | F | F | F | F |
| (BD005) | —CH$_3$ | H | H | Cl | Cl | H | F |
| (BD006) | H | H | H | —NO$_2$ | H | H | —CH$_3$ |
| (BD007) | H | F | H | F | H | H | F |
| (BD008) | H | H | H | —CH$_3$ | H | Cl | H |
| (BD009) | F | H | H | Cl | H | F | H |
| (BD010) | —NO$_2$ | H | H | Cl | Cl | H | Cl |

(Scheme 1)

3-Acetyl-4-methyl sulfoxy(or sulfone)-2-quinolinone (synthesized by the procedure described in Korean Pat. No. 574351) and amine compounds were reacted in solvents with boiling points of more than 100° C. with heating as represented by the Scheme 1. The inert solvent having boiling points of 160-250° C. such as o-dichlorobenzene, diphenylether, N-methylpyrrolidinone and tetrahydrofuran could be used as solvents (particularly, the preparatory process of 3-acetyl-4-methyl sulfoxy(or sulfone)-2-quinolinone could be found in Korean Pat. No. 574351, and that of the compound of the formula 4 in Korean Pat. Nos. 613688 and 613690).

More specifically, 3-acetyl-4-methyl sulfoxy-2-quinolinone (0.01 mole) (prepared by processes described in Korean Pat. No. 574351, e.g., 3-acetyl-6-chloro-8-trifluormethyl-4-methyl sulfoxy-2-quinolinone) and amine (0.01 mole, e.g., 2-phenylethylamine) were refluxed for 4 hr in 50 ml of tetrahydrofuran. After completion of reaction, solvents were removed by a vacuum distillation and the resulting solids were dissolved in 10 ml of ethylacetate, followed by recrystallization with 30 ml of hexane for yielding products of interest.

NMR data of the compound represented by the formula 4 are summarized:

TABLE 5

| Compound ID | $^1$H NMR(CDCl$_3$, 200 MHz, ppm) |
|---|---|
| (BD001) | 13.02(s, 1H), 8.42(s, 1H), 7.72-7.26(s, 6H), 2.80(s, 3H) |
| (BD002) | 13.15(s, 1H), 10.88(s, 1H), 8.66(s, 1H), 8.43(s, 1H), 7.47-7.26(m, 3H), 2.85(s, 3H), 2.46(s, 3H) |
| (BD003) | 13.11(s, 1H), 8.15(s, 1H), 7.40(d, J = 8.4 Hz, 1H), 7.25-7.17(m, 2H), 6.98(d, J = 8.4 Hz, 1H), 2.86(s, 3H), 2.79(s, 3H) |
| (BD004) | 13.33(s, 1H), 7.81-7.08(m, 5H), 2.84(s, 3H) |
| (BD005) | 13.04(s, 1H), 8.07(s, 1H), 7.52-7.17(m, 4H), 6.96(d, J = 8.2 Hz, 1H), 2.86(s, 3H), 2.80(s, 3H) |
| (BD006) | 13.06(s, 1H), 11.02(s, 1H), 8.65(s, 1H), 8.42(s, 1H), 7.39(d, J = 8.2 Hz, 2H), 7.25(d, J = 8.2 Hz, 2H), 2.84(s, 3H), 2.46(s, 3H) |

TABLE 5-continued

| Compound ID | $^1$H NMR(CDCl$_3$, 200 MHz, ppm) |
|---|---|
| (BD007) | 13.08(s, 1H), 7.79-7.04(m, 7H), 2.81(s, 3H) |
| (BD008) | 13.16(s, 1H), 8.20-7.20(m, 7H), 2.73(s, 3H), 2.47(q, J = 7.5 Hz, 2H), 1.19(t, J = 7.5 Hz, 3H) |
| (BD009) | 13.22(s, 1H), 8.45(s, 1H), 7.56-6.86(m, 6H), 2.81(s, 3H) |
| (BD010) | 13.42(s, 1H), 7.66(d, J = 8.4 Hz, 1H), 7.19(d, J = 8.4 Hz, 1H), 6.99-6.89(m, 3H), 2.76(s, 3H) |

Preparative Example 2

Compound Preparation 2

The compounds represented by the following Formula 5 were synthesized according to the Scheme 2:

(5)

TABLE 6

| Compound ID | R$_5$ | R$_6$ | R$_7$ |
|---|---|---|---|
| (BD030) | H | H | H |
| (BD031) | Cl | H | Cl |

(Scheme 2)

Preparative Example 2-1

Synthesis of 6,8-dichloro-4-oxo-2-phenylamino-1,4-dihydro-quinoline-3-carboxylic acid (2,4-dichloro-phenyl)-amide (Compound 5, KSI-3545)

Step 1: Synthesis of N,N'-bis-(2,4-dichloro-phenyl)-malonamide (Compound 1 in Scheme)

A mixture of diethyl malonate (24 g, 0.15 mol) and 2,4-dichloro aniline (60.8 g, 2.5 eq) was heated at 200° C. upon passing nitrogen gas stream to distil out ethanol. Six hours later, the reactants were cooled to room temperature with adding diethylether. The solids produced were filtered and washed with diethylether (yield: 48 g, 82%): $^1$H NMR (CDCl$_3$) δ10.04 (s, 2H) 8.04 (d, J=9 Hz, 2H) 7.42 (m, 2H) 7.26, (dd, J=2.4, 9 Hz, 2H) 3.74 (s, 2H)

Step 2: Synthesis of 2-(bis-methylsulfanyl-methylene)-N,N'-bis-(2,4-dichloro-phenyl)-malonamide (Compound 2 in Scheme)

N,N'-bis-(2,4-dichloro-phenyl)-malonamide (Compound 1 in Scheme, 24 g, 61.2 mmol) and potassium carbonate (25.2 g, 3 eq) were introduced into a flask and dimethylformamide was further added, followed by agitation at 0° C. To the resultant, carbon disulfide (4.9 g, 1.05 eq) was added and after 30 min, iodomethane (17.8 g, 2.05 eq) was added dropwise. The reactants were poured in ice water, filtered, washed with water and normal hexane, and dried under vacuum. The resultant was used without further purification for next steps (yield: 17 g, 56%): $^1$H NMR (CDCl$_3$/DMSO-d$_6$) δ 8.93 (bs, 2H) 8.479d, J=8.7 Hz, 2H) 7.40 (d, J=2.4 Hz, 2H) 7.27 (dd, J=2.4, 8.7 Hz, 2H) 2.51 (s, 6H)

Step 3: Synthesis of 6,8-dichloro-2-methylsulfanyl-4-oxo-1,4-dihydro-quinoline-3-carboxylic acid (2,4-dichloro-phenyl)-amide (Compound 3 in Scheme)

To a flask, 2-(bis-methylsulfanyl-methylene)-N,N'-bis-(2,4-dichloro-phenyl)-malonamide (Compound 2 in Scheme, 1.9 g, 3.83 mmol) was added and then diphenyl ether was added, followed by heating for 2 hr at 250° C. The reactants were cooled to room temperature, filtered, washed with normal hexane and dried under vacuum. The resultant was used without further purification for next steps (yield: 1.13 g, 65.8%): $^1$H NMR (DMSO-d$_6$) δ14.4 (bs, 1H) 8.68 (d, J=9 Hz, 1H) 8.27 (s, 1H) 8.08 (m, 1H) 7.57 (bs, 1H) 7.54 (m, 1H) 7.37-7.00 (m, 1H) 2.63 (s, 3H)

Step 4: Synthesis of 6,8-dichloro-2-methanesulfinyl-4-oxo-1,4-dihydro-quinoline-3-carboxylic acid (2,4-dichloro-phenyl)-amide (Compound 4 in Scheme)

6,8-Dichloro-2-methylsulfanyl-4-oxo-1,4-dihydro-quinoline-3-carboxylic acid (2,4-dichloro-phenyl)-amide (Compound 3 in Scheme, 1.13 g, 2.52 mmol) in acetic acid was mixed with 30% hydrogen peroxide (0.57 g, 2 eq) and heated at 70-80° C. for 2 days upon agitation. The reactants were poured into iced water, filtered, washed with water and normal hexane and dried under vacuum. The resultant was used without further purification for next steps (yield: 1.1 g, 94%): $^1$H NMR (DMSO-d$_6$) δ12.66 (bs, 1H) 8.54-8.19 (m, 4H) 7.61-7.41 (m, 2H) 3.10 (s, 3H)

Step 5: Synthesis of 6,8-dichloro-4-oxo-2-phenylamino-1,4-dihydro-quinoline-3-carboxylic acid (2,4-dichloro-phenyl)-amide (Compound 5 in Scheme, KSI-3545)

To a flask, 6,8-dichloro-2-methanesulfinyl-4-oxo-1,4-dihydro-quinoline-3-carboxylic acid (2,4-dichloro-phenyl)-amide (Compound 4 in Scheme, 1.0 g, 2.15 mmol) and aniline (0.3 g, 1.5 eq) were added and then o-dichlorobenzene was added, followed by heating at 180° C. for 2 hr with agitation. The reactants were cooled to room temperature, filtered, washed with normal hexane and dried under vacuum. The resultant was recrystallized with dimethylformamide to yield the compound 5 (yield: 0.8 g, 75.4%): $^1$H NMR (CDCl$_3$) δ13.50 (s, 1H) 12.99 (s, 1H) 8.62 (s, 1H) 8.47-8.30 (m, 2H) 7.62-7.23 (m, 8H)

Preparative Example 2-2

Synthesis of 6,8-dichloro-2-(2,4-dichloro-phenylamino)-4-oxo-1,4-dihydro-quinoline-3-carboxylic acid (2,4-dichloro-phenyl)-amide (Compound 6, KSI-3548)

6,8-dichloro-2-methanesulfinyl-4-oxo-1,4-dihydro-quinoline-3-carboxylic acid (2,4-dichloro-phenyl)-amide (Compound 4 in Scheme, 1.0 g, 2.15 mmol) prepared in Step 4 of Preparative Example 2-1 and dichloroaniline (0.52 g, 1.5 eq) were introduced into a flask, and o-dichlorobenzene was added, followed by heating at 180° C. for 2 hr with agitation. The reactants were cooled to room temperature, filtered, washed with normal hexane and dried under vacuum. The resultant was recrystallized with dimethylformamide to yield the compound 6 (yield: 0.88 g, 72.8%): $^1$H NMR (CDCl$_3$) δ 13.45 (s, 1H) 13.23 (s, 1H) 8.45 (d, J=8.7 Hz, 1H) 8.30 (d, J=2.1 Hz, 1H) 7.68-7.26 (m, 7H)

Experimental Example 1

Analysis of Inhibition of Vascular Smooth Muscle Cell Proliferation

Human vascular smooth muscle cells (SMC, Bio-whittaker, USA) were plated in 100 μl of DMEM (Dulbelcco's Modified Eagle Medium) containing 10% FBS (fetal bovine serum) in 96-well plates at 5×10$^3$ cells/well and cultured for 24 hr at 37° C. under 10% CO$_2$ atmosphere. Afterwards, cells were starved in 100 μl of DMEM containing 0.2% FBS for 72 hr. Then, cells were incubated in 100 μl of DMEM containing 5% FBS supplemented with 5 ng/ml PDGF (platelet derived growth factor, ProSpec, Israel) and then treated with indicated concentrations of chemicals in DMSO synthesized in Examples. The final concentration of DMSO was adjusted to 1%. After 48-hr treatment, medium was changed with a fresh 5% FBS DMEM and 10 μl/well of premix WST-1 (Takara, Japan) was added for analyzing cell proliferation, followed by 2-hr incubation. Using a ELISA microplate reader, the OD (optical density) values at 450 nm were measured. Compared with no-treatment control, the compounds of this invention were evaluated in terms of their cell proliferation activity. IC$_{50}$ values to vascular smooth muscle cells were calculated based on the OD values and summarized in Table 7.

Experimental Example 2

Analysis of Cytotoxicity to Tumor Cells

To verify whether the compounds of this invention could be used as anticancer agents, their cytotoxicity against tumor cells were examined. NCI-H460 (lung cancer cell line, ATCC, USA) and MDA-MB 435S (breast cancer cell line, ATCC, USA) were used. The cancer cell lines were plated in 100 μl of DMEM (Dulbelcco's Modified Eagle Medium) containing 10% FBS (fetal bovine serum) in 96-well plates at 5×10$^3$ cells/well and cultured for 24 hr at 37° C. under 10% CO$_2$ atmosphere. After change of medium with 100 μl of DMEM containing 5% FBS, cells were treated with the indicated concentration of the compounds in DMSO. The final concentration of DMSO in medium was adjusted to 1%. Following 48-hr treatment, medium was changed with a fresh 5% FBS DMEM and 10 μl/well of premix WST-1 (Takara, Japan) was added for analyzing cell proliferation, followed by 2-hr incubation. Using a ELISA microplate reader, the OD (optical density) values at 450 nm were measured. Compared with no-treatment control, the compounds of this invention were evaluated in terms of their cytotoxicity to cancer cell lines. IC$_{50}$ values to cancer cell lines were calculated based on the OD values and summarized in Table 7.

TABLE 7

| Compound ID | IC$_{50}$ (μM) | | |
| --- | --- | --- | --- |
| | SMC | NCI-H460 | MDA-MB 435S |
| (BD001) | 0.21 | 1.5 | 1.8 |
| (BD002) | 0.063 | 0.4 | 0.3 |
| (BD003) | 0.065 | 0.4 | 0.6 |
| (BD004) | 0.067 | 0.85 | 0.9 |
| (BD005) | 0.28 | 0.6 | 25 |
| (BD006) | 0.8 | 1.5 | 1.1 |
| (BD007) | 0.29 | 1.6 | 1.1 |
| (BD008) | 1.64 | 7.2 | 6.4 |
| (BD009) | 0.625 | 2.6 | 5.2 |
| (BD010) | 6.5 | 25 | 12 |
| (BD030) | 0.03 | 1 | 0.3 |
| (BD031) | 0.016 | 0.21 | <0.16 |
| (BD032)[1] | 0.14 | 3.3 | 3.5 |
| (BD033)[2] | 0.137 | 3.2 | 4.0 |
| (BD034)[3] | 0.127 | 3.9 | 1.6 |

[1] compound defined by R$_5$ = F, R$_6$ = H, and R$_7$ = Cl in the formula 6
[2] compound defined by R$_5$ = Cl, R$_6$ = Cl, and R$_7$ = H in the formula 6
[3] compound defined by R$_5$ = H, R$_6$ = F, and R$_7$ = F in the formula 6

As represented in Table 7, the compounds of this invention exhibit much lower IC$_{50}$ values to vascular smooth muscle cells, demonstrating that the compounds effectively inhibit proliferation of vascular smooth muscle cells to be used in chemotherapy of hyperproliferative vascular disorders. Surprisingly, the compounds of ID Nos. BD002, BD003, BD004, BD030 and BD031 were measured to have very low IC$_{50}$ values, less than 1 μM.

Furthermore, the compounds of the present invention also exhibit lower IC$_{50}$ values against cancer cell lines, addressing applicability to anticancer drugs. Interestingly, the compounds of ID Nos. BD002, BD003, BD004, BD030 and BD031 were analyzed to have very low IC$_{50}$ values, less than 1 μM, highlighting their usefulness in chemotherapy of cancers.

Experimental Example 3

Evaluation on Inhibition of Restenosis Using Balloon Injury of Carotid Artery

To examine restenosis inhibition effects of the present compounds, rat restenosis models were constructed using balloon injury of carotid artery.

Sprague-Dawley male rats with body weights of 350±30 g (12-14 week age, DaehanBiolink, Inc., Korea) were adapted to surrounding environments for one week. For each experiment, 7-10 rats were used. Rats were anesthetized by intraperitoneal administration of a mixture of ketamine (70 mg/kg) and xylazine hydrochloride (33 mg/kg) and their (left common carotid artery, CCA) and branches of internal carotid artery (ICA) and external carotid artery (ECA) were exposed by neck central compartment dissection. The proximal portion of the left common carotid artery and distal portion of the internal carotid artery were temporarily ligated with suture to block bloodstream, the distal portion of the external carotid artery was ligated. The wall of the external carotid artery between both sutures was partially dissected. 2F Fogarty balloon (Edwards Lifesciences) was inserted and the ligation of the left common carotid artery was then unraveled, followed by advancing the balloon along the direction of the ascending aorta. The balloon was inflated and pulled out at the extent that resistance was allowed at the terminal portion of the common carotid artery of the aortic arch, such that the lesion of the left common carotid artery was induced. The process for lesion was repeated three times and then the Fogarty balloon was removed. These procedures induced vascular endothelial removal to damage vascular smooth muscle, resulting in intima thickening. The external carotid artery was permanently ligated with suture and ligation between the common carotid artery and the internal carotid artery was temporarily unraveled for reperfusion. Blood perfusion was observed and dissected portions were ligated. Following the operation, the present compound (BD-030) dispersed in polyoxyethylated castor oil was intraperitoneally administered to rats. Rats were recovered from anesthetization and put into separate cages for maintenance.

Afterwards, the perfusion fixation and histological examinations were performed.

Two weeks after carotid artery injury, ketamine was intraperitoneally administered for anesthetization, both carotid veins were dissected and physiological saline was perfused through aorta for pressure-fixation. The injured left common carotid artery and the non-injured right common carotid artery were extracted and fixed for 12 hr in 10% formalin solution, followed by paraffinization. The sections having 3 μm-thickness were prepared from the most proliferative parts in injured portions, the right common carotid artery was used as controls. Each tissue sample was stained by a hemotoxylin-eosin staining method for observing neointima thickening.

Figure 1A:
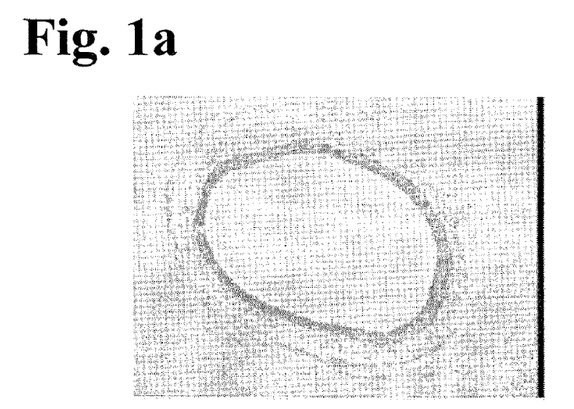
FIG. 1*a* is represents histological images of the non-balloon-injured right common carotid artery.
Figure 1B:
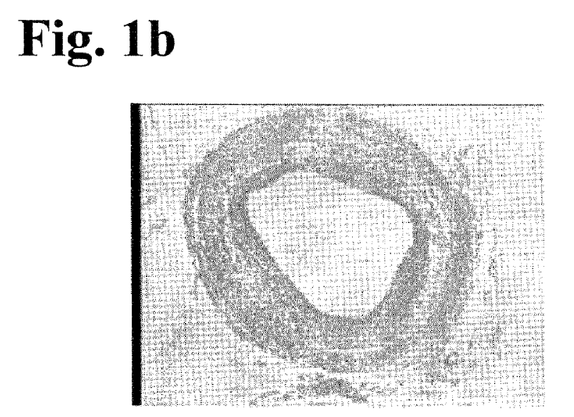
FIG. 1*b* represents histological images of the balloon-injured left common carotid artery.
Figure 1C:
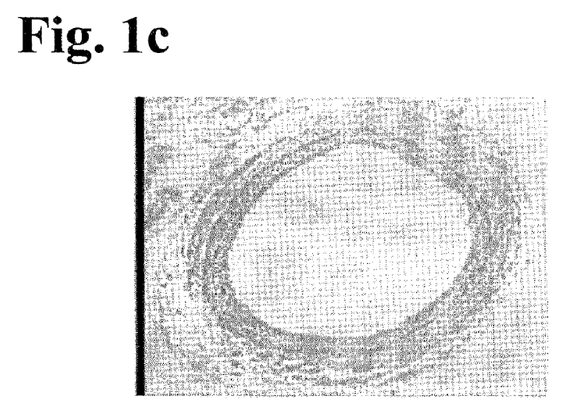
FIG. 1*c* is shows histological observations of the left common carotid artery 2 weeks post-administration of the compound administration after balloon injury.

FIG. 1a represents the non-balloon-injured right common carotid artery and FIG. 1b represents the balloon-injured left common carotid artery. FIG. 1c shows histological observations of the left common carotid artery 2 weeks post-administration of the compound administration after balloon injury. As shown in FIG. 1c, the compound administration after balloon injury clearly shows the reduced neointima thickening by about 80% compared with the balloon-injured left common carotid artery (FIG. 1b), while the compound administration shows a slightly increased neointima thickening compared with the non-balloon-injured right common carotid artery as controls (FIG. 1a).

The present invention provides a composition for inhibiting proliferation of smooth muscle cells, a pharmaceutical composition for preventing or treating hyperproliferative vascular disorders and a pharmaceutical anticancer composition. As demonstrated in Examples, the present compounds exhibit IC$_{50}$ values of less than 0.03 μM and 0.16 μM for vascular smooth muscle cells and cancer cells, respectively to effectively prevent proliferation of vascular smooth muscle cells and cancer cells, thereby ensuring prevention or treatment of hyperproliferative vascular disorders such as arteriosclerosis and restenosis, and cancers.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating or reducing the development of a hyperproliferative vascular disorder, which comprises administering to a subject a pharmaceutical composition comprising: (a) a pharmaceutically effective amount of a compound represented by Formula 2 or a pharmaceutically acceptable salt thereof, (2)

wherein $R_1$, $R_2$, $R_3$, $R_4$, $R_5$, $R_6$ and $R_7$ independently represent hydrogen, halo, nitro or $C_1$-$C_{12}$ alkyl; Z represents $C_1$-$C_{12}$ alkyl or —NH—$R_8$; and $R_8$ represents halo-substituted phenyl; and (b) a pharmaceutically acceptable carrier.

2. The method according to claim 1, wherein the compound or a pharmaceutically acceptable salt thereof is represented by Formula 3:

(3)

wherein $R_1$, $R_2$, $R_3$, $R_4$, $R_5$, $R_6$ and $R_7$ independently represent hydrogen, halo, nitro or $C_1$-$C_{12}$ alkyl.

* * * * *